United States Patent
Gur

(10) Patent No.: US 7,453,080 B2
(45) Date of Patent: Nov. 18, 2008

(54) SYSTEM FOR LOCATING A PHYSICAL ALTERATION IN A STRUCTURE AND A METHOD THEREOF

(75) Inventor: Joshua Gur, Jerusalem (IL)

(73) Assignee: Israel Aerospace Industries Ltd., Lod (IL)

(*) Notice: Subject to any disclaimer, the term of this patent is extended or adjusted under 35 U.S.C. 154(b) by 0 days.

(21) Appl. No.: 11/791,720

(22) PCT Filed: Nov. 28, 2005

(86) PCT No.: PCT/IL2005/001269

§ 371 (c)(1),
(2), (4) Date: May 29, 2007

(87) PCT Pub. No.: WO2006/056997

PCT Pub. Date: Jun. 1, 2006

(65) Prior Publication Data

US 2008/0023635 A1    Jan. 31, 2008

(30) Foreign Application Priority Data

Nov. 28, 2004    (IL) .................................. 165415

(51) Int. Cl.
*G01N 21/86* (2006.01)
(52) U.S. Cl. ................. 250/559.4; 250/559.45
(58) Field of Classification Search .............. 258/559.4, 258/559.42, 559.43, 555.44, 559.45, 559.46, 258/221; 356/430, 238.1, 238.2, 237.1–237.5; 340/651–653

See application file for complete search history.

(56) References Cited

U.S. PATENT DOCUMENTS

| 4,389,575 | A | * | 6/1983 | Cole .................... 250/559.47 |
| 4,399,430 | A | | 8/1983 | Kitchen |
| 5,307,152 | A | | 4/1994 | Boehnlein et al. |
| 5,592,149 | A | | 1/1997 | Alizi |
| 6,259,526 | B1 | | 7/2001 | Pace et al. |
| 6,462,820 | B1 | | 10/2002 | Pace et al. |
| 2004/0225480 | A1 | | 11/2004 | Dunham |

* cited by examiner

*Primary Examiner*—Que T Le
(74) *Attorney, Agent, or Firm*—The Nath Law Group; Jerald L. Meyer; Derek Richmond

(57) ABSTRACT

There is provided a system and method for locating a physical alteration, if such exists, in a structure having a substantially planar surface comprising a plurality of elements capable of scattering electro-magnetic radiation and openings arranged between the elements, according to one embodiment, the system comprises a moving platform for providing relative motion of the system with respect to the structure; at least one source of coherent electro-magnetic radiation configured for illuminating at least a portion of said surface in its relative motion with respect to the structure; at least a first and a second detection unit each operable along a different collection direction and configured for collecting electro-magnetic radiation reflected from said at least a portion of the surface and for generating an intensity pattern of the reflected radiation indicative of an arrangement of the elements and openings; and a computing unit configured for generating a segmented map of the portion based on said intensity patterns, by associating each segment with location data indicative of the location of the segment and occurrence data indicative of an occurrence of the alteration, thereby allowing to compare said map to a reference model and determine the location of the alteration, if such exists.

22 Claims, 13 Drawing Sheets

US 7,453,080 B2

SYSTEM FOR LOCATING A PHYSICAL ALTERATION IN A STRUCTURE AND A METHOD THEREOF

FIELD OF THE INVENTION

This invention relates to systems and methods for locating physical alterations and variations in a structure and specifically for structures having a substantially planar surface comprising a plurality of elements capable of scattering electro-magnetic radiation and openings arranged between the elements, e.g. fences.

BACKGROUND OF THE INVENTION

The need for detecting and locating physical alterations is known e.g. in manufacturing and monitoring of structures like PCBs (Printed Circuit Boards), semiconductor wafers, fabrics, and security fences. Such structures are exposed to alterations like in-continuities (e.g. cut-offs), random or non-random irregularities, disruptions, bending, or any other physical change in the structure.

According to one known approach, the occurrence of an alteration in a structure is checked with respect to a reference. For example, in the field of printed electronic components, there are known procedures for scanning a surface and comparing the scanned sample to a reference model. Another known approach, suitable for a structure with a predefined design (e.g. wired structure), is to detect that the structure follows the design rules, e.g. the distance between the wires, wire width, permitted radius of curvature.

These methods are not suitable for very long structures such as fences and textiles, because the required reference model is extremely large and thus problems specific to very long surfaces arise, such as the need for large computer memory volumes to store the reference model and strong processors. Likewise, there are structures that are not characterized by precise design rules to which reference can be made to examine a deviation that indicates a change.

There is, accordingly, a need in the art for a system and method for detecting and locating variations and alterations present in long and/or large structures, that will overcome the problems indicated above.

SUMMARY OF THE INVENTION

According to one embodiment, the present invention provides for a system for locating a physical alteration, if such exists, in a structure having a substantially planar surface comprising a plurality of elements capable of scattering electro-magnetic radiation and openings arranged between the elements, the system comprising:
- a moving platform for providing relative motion of the system with respect to the structure;
- at least one source of coherent electro-magnetic radiation configured for illuminating at least a portion of said surface in its relative motion with respect to the structure;
- at least a first and a second detection unit each operable along a different collection direction and configured for collecting electro-magnetic radiation reflected from said at least a portion of the surface and for generating an intensity pattern of the reflected radiation indicative of an arrangement of the elements and openings;
- a computing unit configured for generating a segmented map of the portion based on said intensity patterns, by associating each segment with location data indicative of the location of the segment and occurrence data indicative of an occurrence of the alteration, thereby allowing to compare said map to a reference model and determine the location of the alteration, if such exists.

According to another embodiment, the present invention provides for a method for detecting and locating an alteration in a structure having a substantially planar surface formed by a plurality of elements capable of scattering electro-magnetic radiation and openings arranged between the elements, the method comprising:
- collecting, along at least two different collection directions, electro-magnetic radiation reflected from a portion of the structure illuminated at least by one coherent radiation source in a relative motion with respect to the structure, and generating an intensity pattern of the reflected radiation indicative of an arrangement of the elements and openings;
- generating a segmented map of the portion based on said intensity pattern, by associating each segment with location data indicative of its location and occurrence data indicative of an occurrence of the alteration, if such exists.

According to another embodiment, the present invention provides for a method for detecting and locating an alteration in a structure having a substantially planar surface formed by a plurality of elements capable of scattering electro-magnetic radiation and openings arranged between the elements, the method comprising:
- collecting, along at least two different collection directions, electro-magnetic radiation reflected from a portion of the structure illuminated at least by one coherent radiation source in a relative motion with respect to the structure, and generating an intensity pattern of the reflected radiation indicative of an arrangement of the elements and openings;
- generating a segmented map of the portion based on said intensity pattern, by associating each segment with location data indicative of its location and occurrence data indicative of an occurrence of the alteration, if such exists; and
- comparing said map to a reference model and determining the location of the alteration, if such exists.

According to another embodiment, the present invention provides for a method for detecting and locating an alteration in a structure having a substantially planar surface formed by a plurality of elements capable of scattering electro-magnetic radiation and openings arranged between the elements, the method comprising:
- collecting, along at least two different collection directions, electro-magnetic radiation reflected from a portion of the structure illuminated at least by one coherent radiation source in a relative motion with respect to the structure, and
- generating an intensity pattern of the reflected radiation indicative of an arrangement of the elements and openings;
- generating a segmented map of the portion based on said intensity pattern, by associating each segment with location data indicative of its location and occurrence data indicative of an occurrence of the alteration, if such exists; and
- comparing said map to a reference model and determining the location of the alteration, if such exists.
- applying at least one predefined verification rule by analyzing occurrence data associated with different segments.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

The present invention provides for a system and method for locating a physical alteration in a structure. The invention is used preferably for locating a physical alteration, if such exists, in a structure having a substantially planar surface comprising a plurality of elements capable of scattering electro-magnetic radiation (e.g. metal elements) and openings arranged between the elements. Examples of such structures are: fences, fabrics, woven textiles, honeycomb-shape structures, grid-like structures, perforated structures and the like.

According to certain embodiments; the invention provides for systems and methods for locating an alteration of about a millimeter in size, along a structure of tens of kilometers long. A suitable structure is characterized by the relation between the openings and elements on its surface. According to some of its embodiments the invention is most suitable for structures having openings covering about 50% of the surface, and also exceeding this percentage. According to some embodiments, the invention is suitable for detecting physical alterations in structures having openings of a size substantially in the millimeter range and above.

For simplicity of explanation, the principles of the present invention will be disclosed in the following, mainly with respect to detection of alterations in fences, and more specifically fences of the type used to border and secure an area (e.g. a wired fence, a welded wire fence, a barbed fence, a fence having wires supported by spaced apart posts, and more). Such fences are typically construed by horizontally stretched wires supported by vertically, spaced apart posts. Physical alterations in such a fence may be a cut made in a wire, a bend of wire or post made during an attempt to break or penetrate the fence, and the like. The alterations of this sort may cause very fine variations in the form of the fence, and accordingly present a serious difficulty in their detection. For some applications, the operational considerations require a resolution in the order of centimeters and even millimeters in detection and localization of the alterations, to be achieved by relatively cheap and sustainable hardware. This requirement is challenging to fulfill, using standard and known image processing techniques and hardware.

Figure 1:
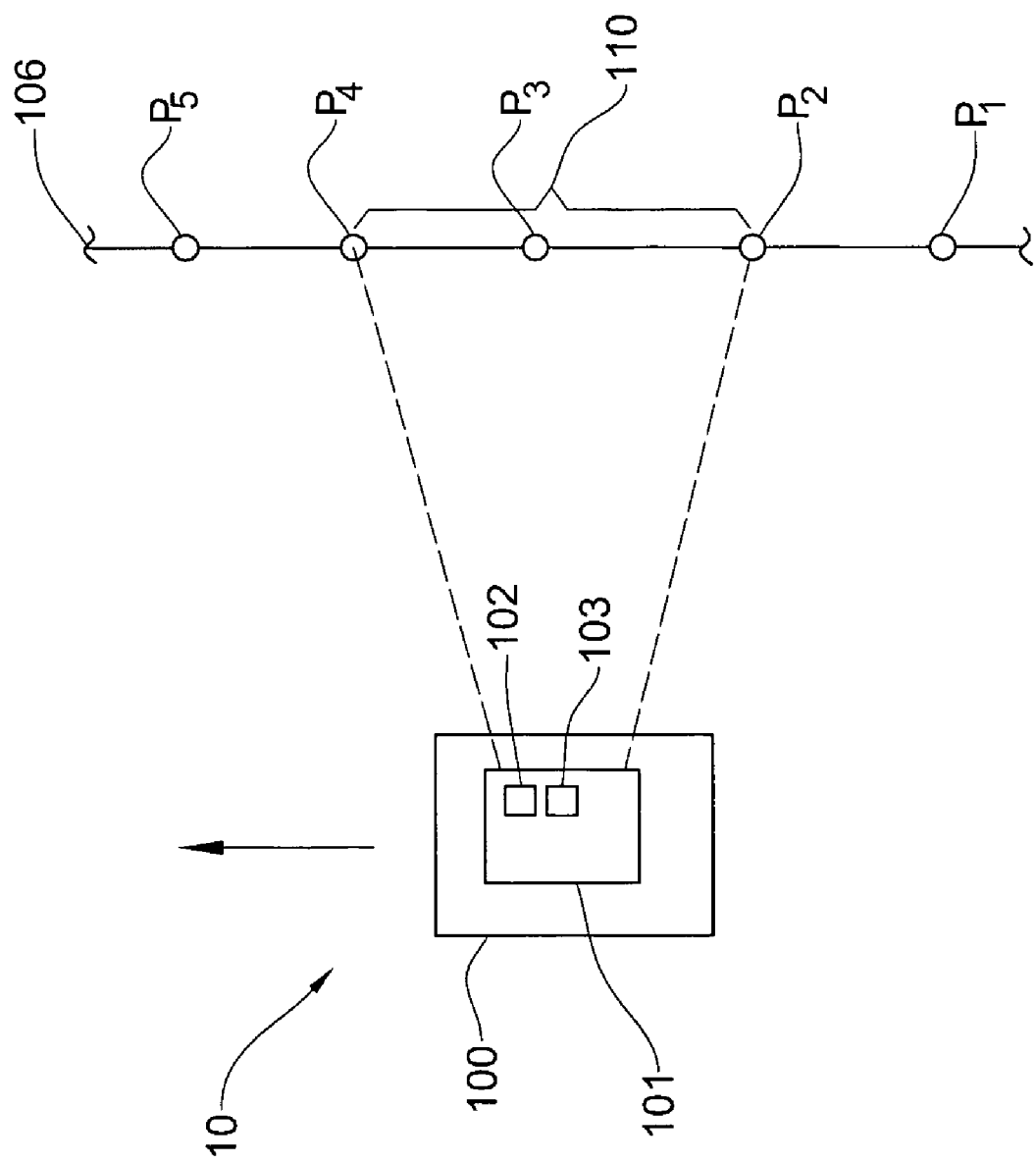
FIG. 1 is a schematic illustration of a system according to an embodiment of the invention.

FIG. 1 is a schematic illustration of a computer-based system 10 according to an embodiment of the invention, for detecting and locating an alteration in a fence 106 having horizontal wire lines (the top view of which is shown in FIG. 1) supported by posts (posts $P_1$-$P_5$ are shown in FIG. 1). In the embodiment shown in FIG. 1, the system 10 comprises, inter-alia, a moving platform 100 (e.g. a jeep, an unmanned automated vehicle, etc.) and a system 101 mounted onboard. The system 10, also referred hereinafter as 'the vehicle', travels along the fence 106 and scans a portion 110 of the fence 106 in order to locate a physical alteration in the form of the fence 106, if such exists.

In the exemplary and non-limiting embodiment illustrated in FIG. 1, fence portion 110 is scanned substantially simultaneously by two detection units 102 and 103 (additional detection units may also be employed, as will be detailed further below). The information gathered by the two detection units is processed to yield an output representing an updated state of the fence (this will be disclosed further below). The output is then compared with a reference model representing a reference state of the fence, with respect to each segment of the fence. Any discrepancy between the updated state and the reference state may indicate an alteration in the fence, such as a cut, a bend of a wire or post, a change in the relative angles between elements of the fence, and the like. These alterations, in turn, may indicate an attempt to tamper with the fence, an attempt to penetrate the fence, an attempt to camouflage cuts and other indications of penetration.

According to an embodiment of the invention, in order to save memory volume and enable efficient data retrieval and very fast processing, substantially each segment of the fence is associated with a 'location data' generated in accordance with information gathered by at least one of the three detection units. The location data is indicative of the location of the segment. The segment is further associated with an 'occurrence data' generated in accordance with information gathered by at least one of the two detection units. The occurrence data is indicative of the occurrence of an alteration in the segment, if such exists. As will be discussed further below, a relatively small quantity of data is needed to be stored and retrieved in order to compare the updated state of the fence with the reference model. According to other embodiments of the invention, various verification rules are applied, e.g. by comparing the occurrence data of certain segments (e.g. adjacent segments of the fence) to enhance credibility of the system. These outcomes are very useful e.g. for real-time operational needs.

Figure 2:
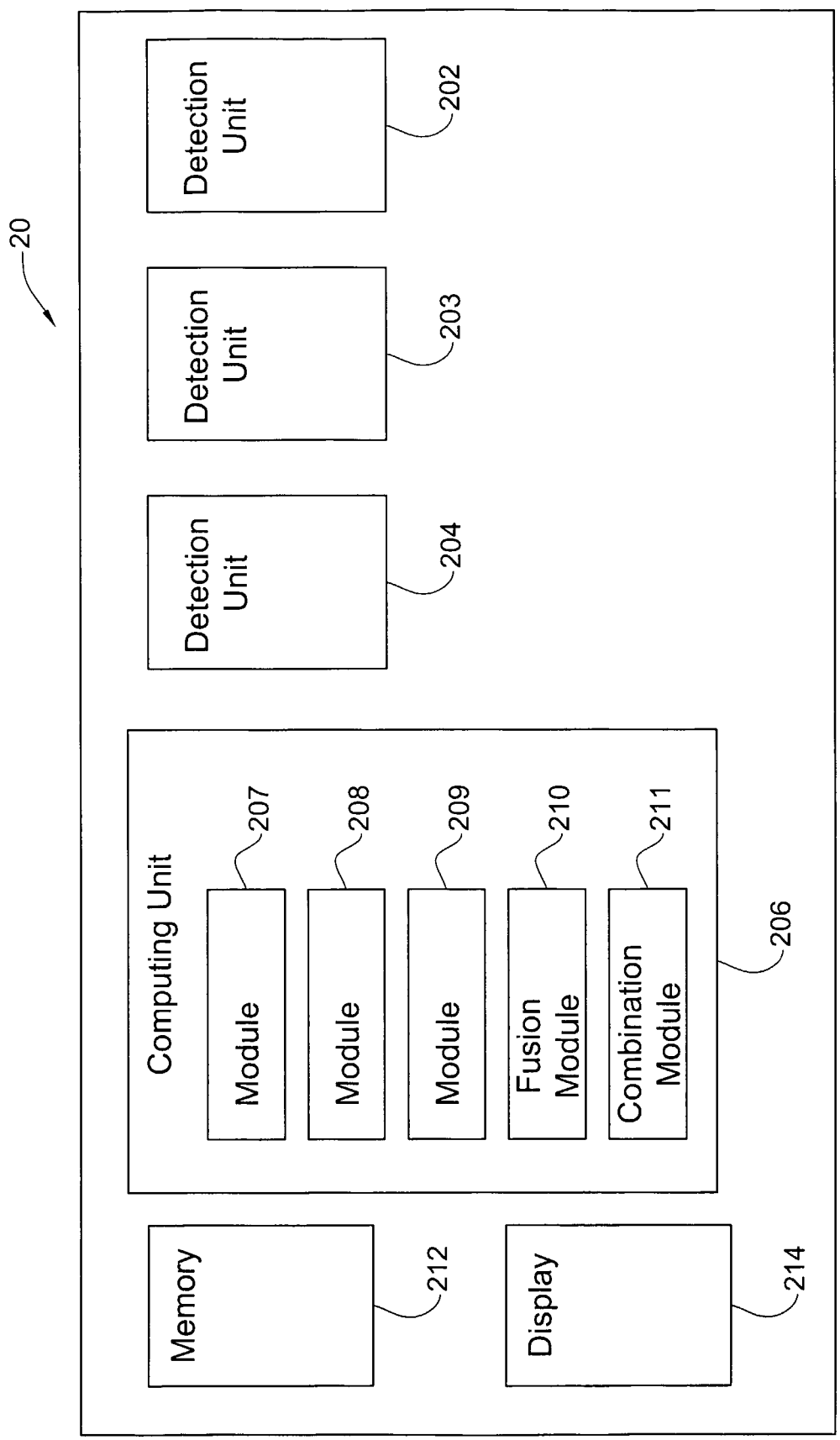
FIG. 2 is another schematic illustration of a system according to an embodiment of the invention.

FIG. 2 is a schematic illustration of a system 20 according to an embodiment of the invention. System 20 is mounted onboard a moving platform which is not shown in FIG. 2. System 20 comprises, inter-alia, three detection units 202, 203 and 204, coupled to a computing unit 206 (also referred to hereinafter as 'the processor'). Also coupled to the processor 206 are a display unit 214, and optionally a communication unit (not shown in FIG. 2). In the embodiment shown in FIG. 2, computing unit 206 serves all components of the system 20, and hence comprises, inler-alia, modules 207-209 for processing data received from the detection units 202-204, indicative of the detected intensity patterns; fusion module 210 for generating the 'location data' and 'occurrence' data based on information received at least from modules 207-209; and combination module 211 for superimposing data corresponding to the detected portion of the fence and for generating an appropriate signal to be fed into display 214.

According to the exemplified embodiment of the invention, the first and second detection units are laser scanners (this embodiment is also referred to as 'double speckle scanning'), each having its own laser source (not shown in FIG. 2) to illuminate a portion of the fence. the laser source could be a commercially available laser, operating un the near IR range or less. The wavelength of the laser affects the spackle reflection coming from the scattering elements. The wavelength of the radiation provided by the laser should be substantially in the order of the irregularity that characterizes the scattering element material, or less.

Units 202 and 203 are adapted to collect electromagnetic radiation reflected from the scattering elements of the fence. Units 202 and 203 operate along different collection directions. For example, unit 202 operates along a direction parallel to the movement direction of the vehicle (e.g. a substantially horizontal collection direction) whereas unit 203 operates along a perpendicular direction (e.g. a substantially vertical collection direction). Put differently, unit 202 is adapted to scan the horizontal wires and unit 203 is adapted to scan the posts. Third detection unit 204 is a video camera system that is adapted to capture an image of the portion of the fence illuminated by the lasers.

In the exemplified and non-limiting embodiment shown in FIG. 2, each of the units 202-204 is coupled to corresponding modules 207-209, accommodated by computing unit 206 for generating a corresponding intensity pattern, indicative of the arrangement of the wires and posts of the fence. This will now be explained with respect to the speckle pattern generated by collecting reflections from the scattering elements of the fence (e.g. metal wires and poles), by detection units 202 and 203.

Figure 3A:
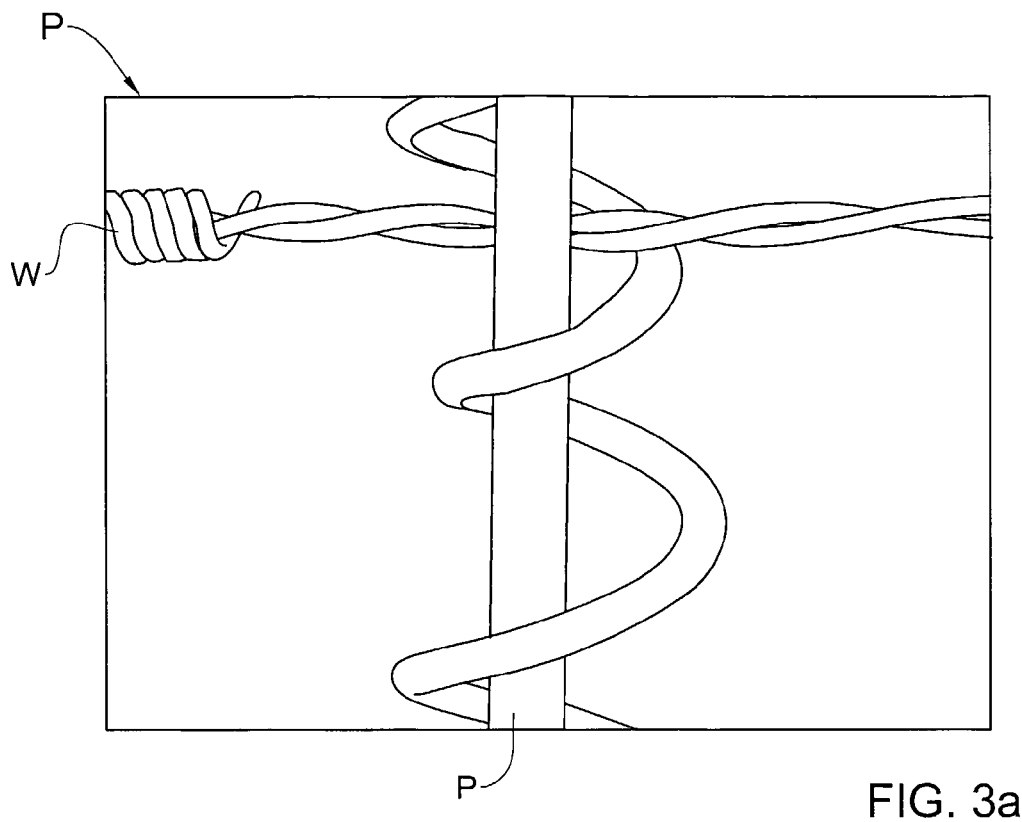
FIGS. 3a-3b are schematic illustrations of an operation carried out according to an embodiment of the invention.
Figure 3B:
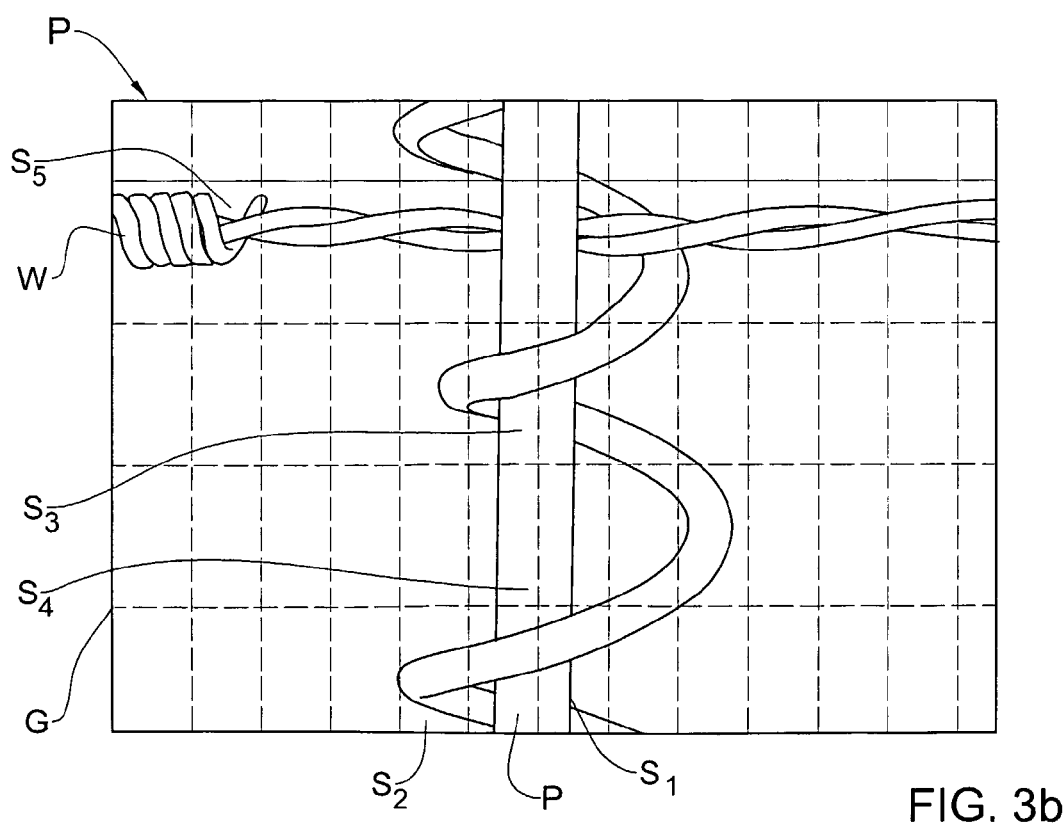
Figure 4A:
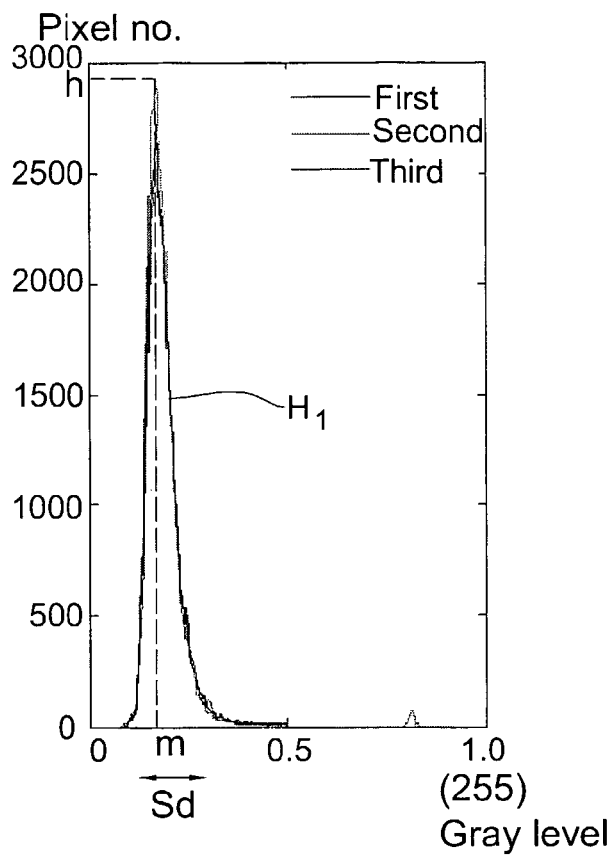
FIGS. 4a-4e are schematic illustrations of another operation carried out according to an embodiment of the invention.
Figure 4A:
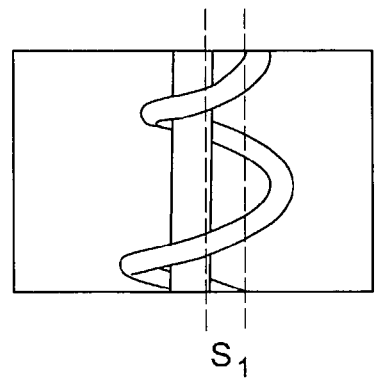
Figure 4B:
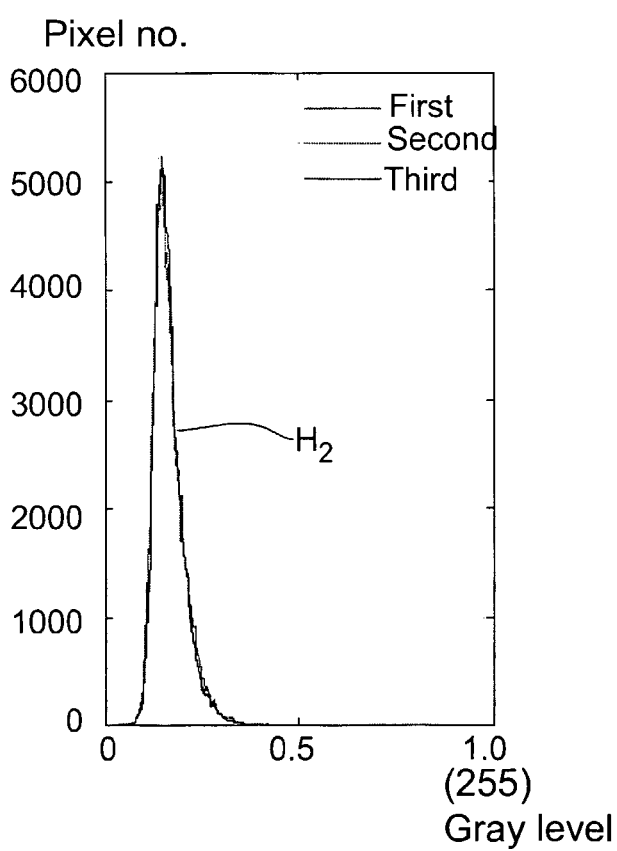
Figure 4B:
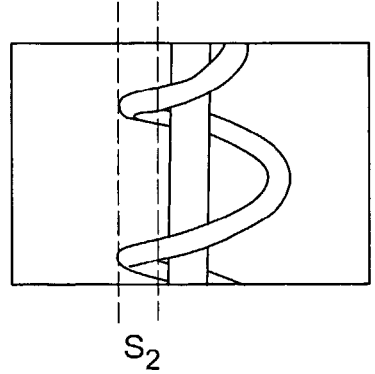
Figure 4C:
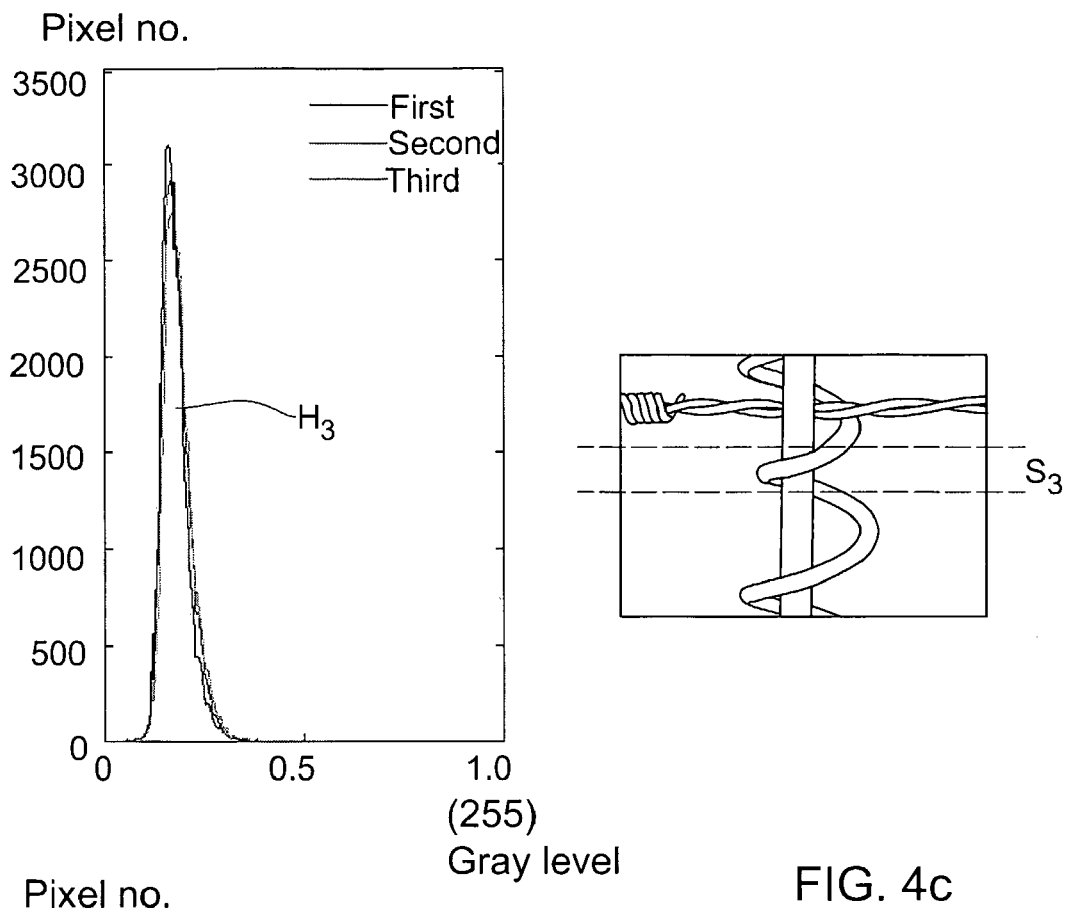
Figure 4D:
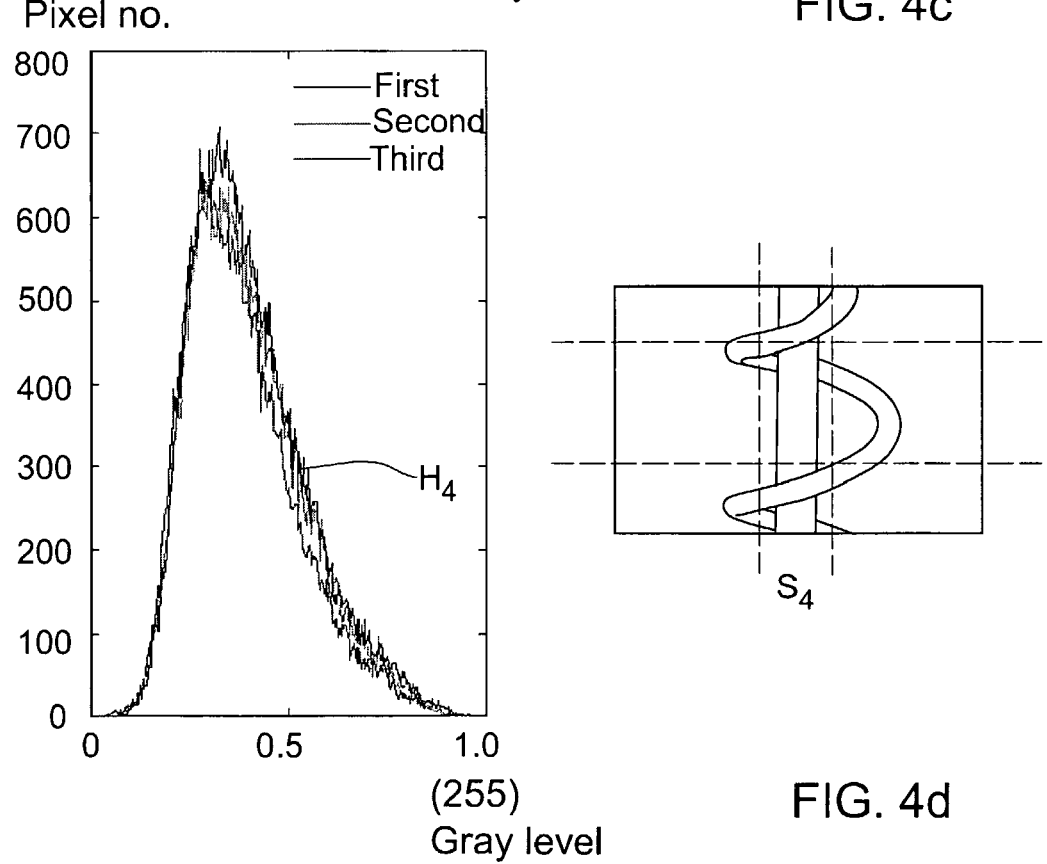
Figure 4E:
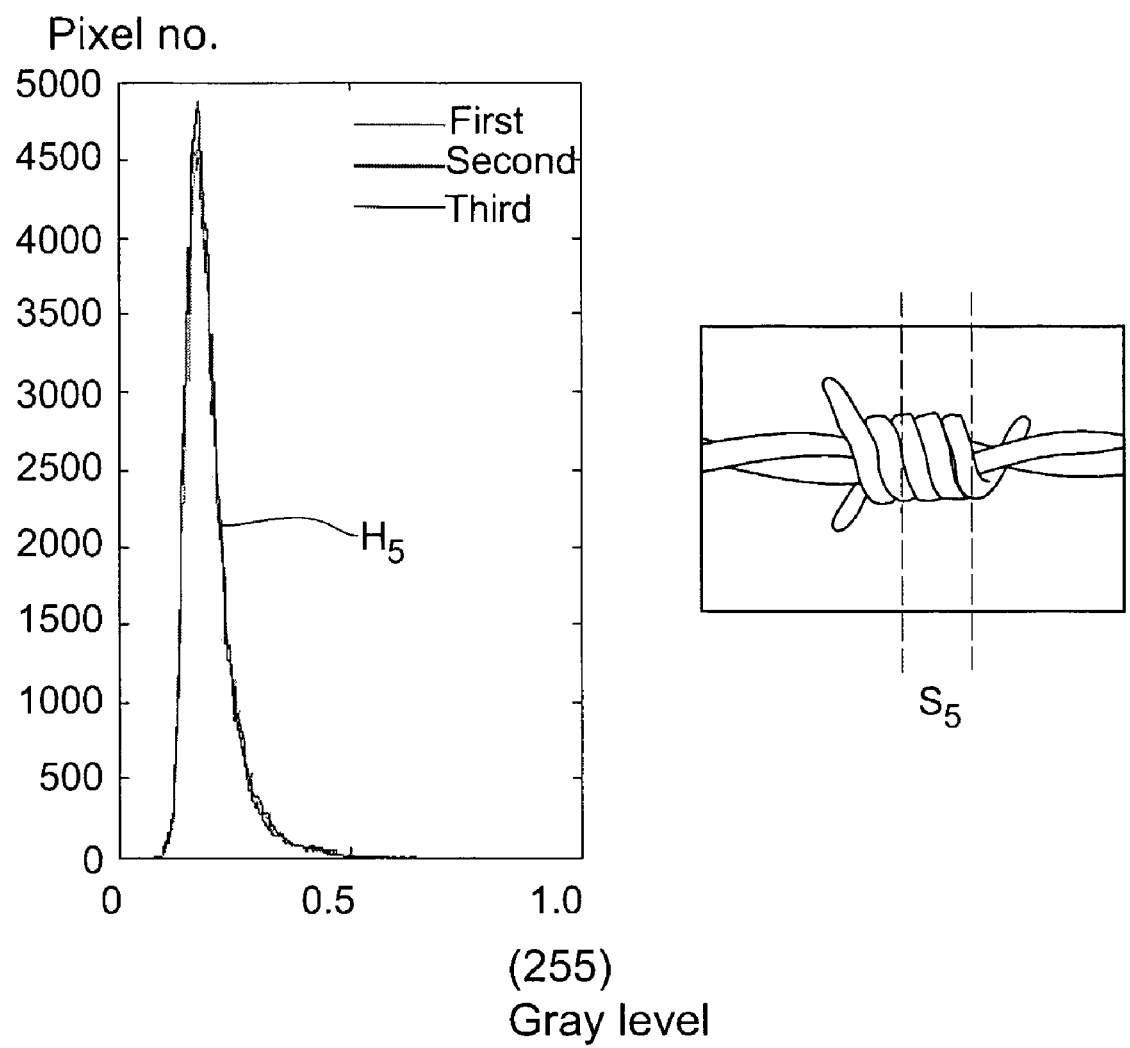

FIG. 3a is an illustration of an image of a portion P of a fence, showing a post and a wire w. FIG. 3b is an illustration of the image of the portion P segmented by a grid G. Several segments $s_1$-$s_5$ are marked. For illustration, the foregoing explanation is presented with respect to an image of the fence portion. This image may be generated by the data collected by the video camera 204, or reconstructed from the data collected by the scanning units 202-203. Note however that in order to detect the fence portion, there is no need to process a corresponding full image. The portion may be mapped based on information indicative of the location of each segment, together with information indicative of the occurrence of an alteration.

Turning now to also to FIGS. 4a-4e, there are illustrated segments $s_1$-$s_5$. Each segment is associated with a contrast histogram (grey level histogram) corresponding to its unique speckle intensity pattern, $H_1$-$H_5$. As illustrated by FIGS. 4a-4e, each segment of a fence element can be associated with a unique speckle intensity pattern corresponding to its structure. The speckle intensity pattern represented by the contrast histograms shown in each of FIGS. 4a-4e is an outcome of three scanning operations, each carried out at three focus conditions of the scanning optics, which represent variations in scanning conditions e.g. focus, relatively small deviations in viewing distance and more occurring e.g. due to movements of the vehicle. As shown, the contrast histograms strongly depend upon the form of the fence segment, while having a weaker dependency on the focus conditions. Hence, the speckle intensity pattern of the radiation reflected from a fence segment provides good indication of the form of that segment. This indication is represented by the contrast histogram and can be represented by a set of parameters characterizing the corresponding distribution function, e.g. mean deviation value m, standard deviation value sd, peak height h, and more. Hence, a set of only few parameters, corresponding to the speckle intensity pattern of radiation reflected from a fence segment, could represent the form of that segment. The set of parameters is considered in constitution of the 'occurrence data' mentioned above with reference to FIG. 1.

Figure 5B:
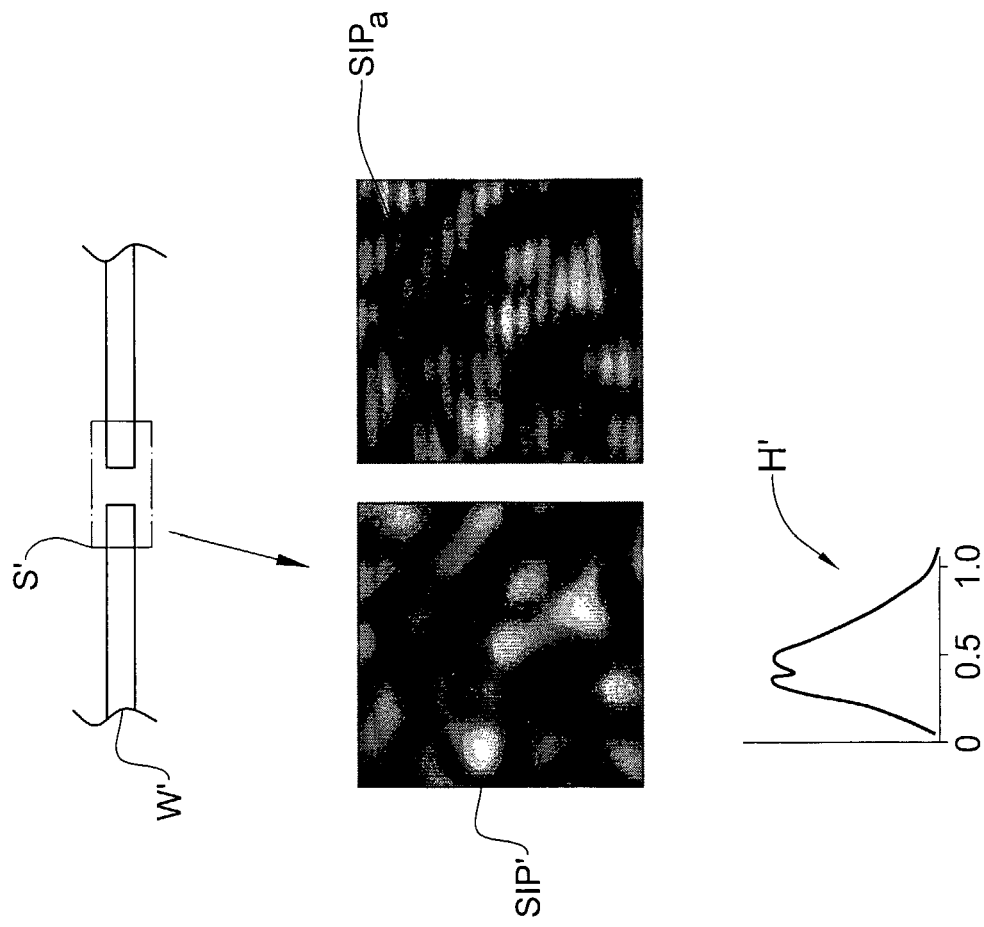
FIGS. 5a-5b are schematic illustrations of an operation carried out according to an embodiment of the invention.
Figure 5A:
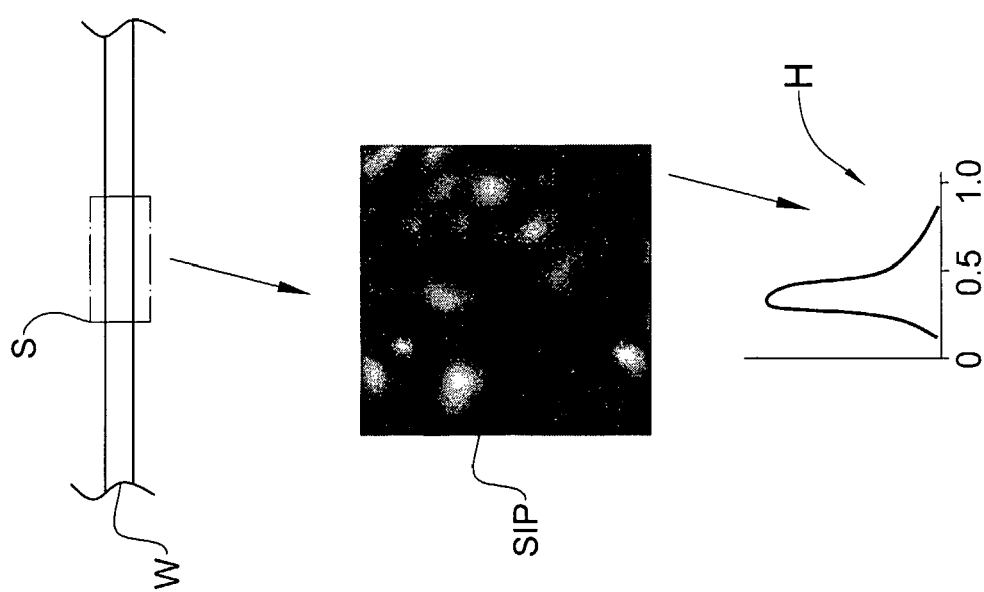

According to an embodiment of the invention, such a set is used for constituting the reference model and the 'occurrence' data corresponding to the fence segment. Discrepancies between the two may indicate a change in the form of the segment. An illustration of an exemplary discrepancy caused by a cut in the fence is shown in FIGS. 5a-5b: in FIG. 5a there are shown a segment s of a wire w, the corresponding speckle intensity pattern SIP and contrast histogram H. In FIG. 5b there are shown a segment s' of a wire w', in which a cut is made, the corresponding speckle intensity pattern SIP' and contrast histogram H', that comprises two peaks, indicating reflections coming from the adjacent cut ends. Pattern SIPa is a representation of a Fourier transform of pattern SIP, clearly showing the double intensity peaks indicating the cut.

The invention is not limited to detection and location of cuts and other alterations due to physical damage in the structure. The invention is useful for detecting an alteration which indicates a variation in the form of the structure, such as a bend in a wire or a post. Such variations are detected by comparing an updated speckle intensity pattern with a reference speckle intensity pattern (e.g. as created by a provisioning operation), corresponding substantially to the same segment of the fence. Assuming for example, that FIG. 4a relates to a segment s of a post as scanned during e.g. the provisioning operation. Segment s is represented by a set of parameters that characterizes histogram $H_1$. Now, if just prior to an update operation, the post is bent e.g. due to a penetration attempt, less speckle intensity may be collected with respect to segment s. As a result, a discrepancy between the reference model and the updated data is revealed—different values of the characterizing parameters are obtained and associated with segment s, thereby giving rise to a detected alteration.

The above procedure is conditioned by the accuracy and resolution of the localization of segment s: without ensuring that the updated and reference 'occurrence data' relates substantially to the same segment, less importance, or none at all, should be given to the discrepancies between the updated and reference speckle intensity patterns. The present invention provides for high accuracy localization of a segment, u to a resolution of few centimeters and millimeters along a 50 km long fence.

According to an embodiment of the invention, highly accurate localization is achieved by locating a segment in respect to an adjacent post, and uniquely identifying the post e.g. by its serial number—this information is considered in constitution of the 'location data' (referred to above with reference to FIG. 1) that characterizes a segment, which in turn allows for accurate and fast localization of each segment.

Figure 6:
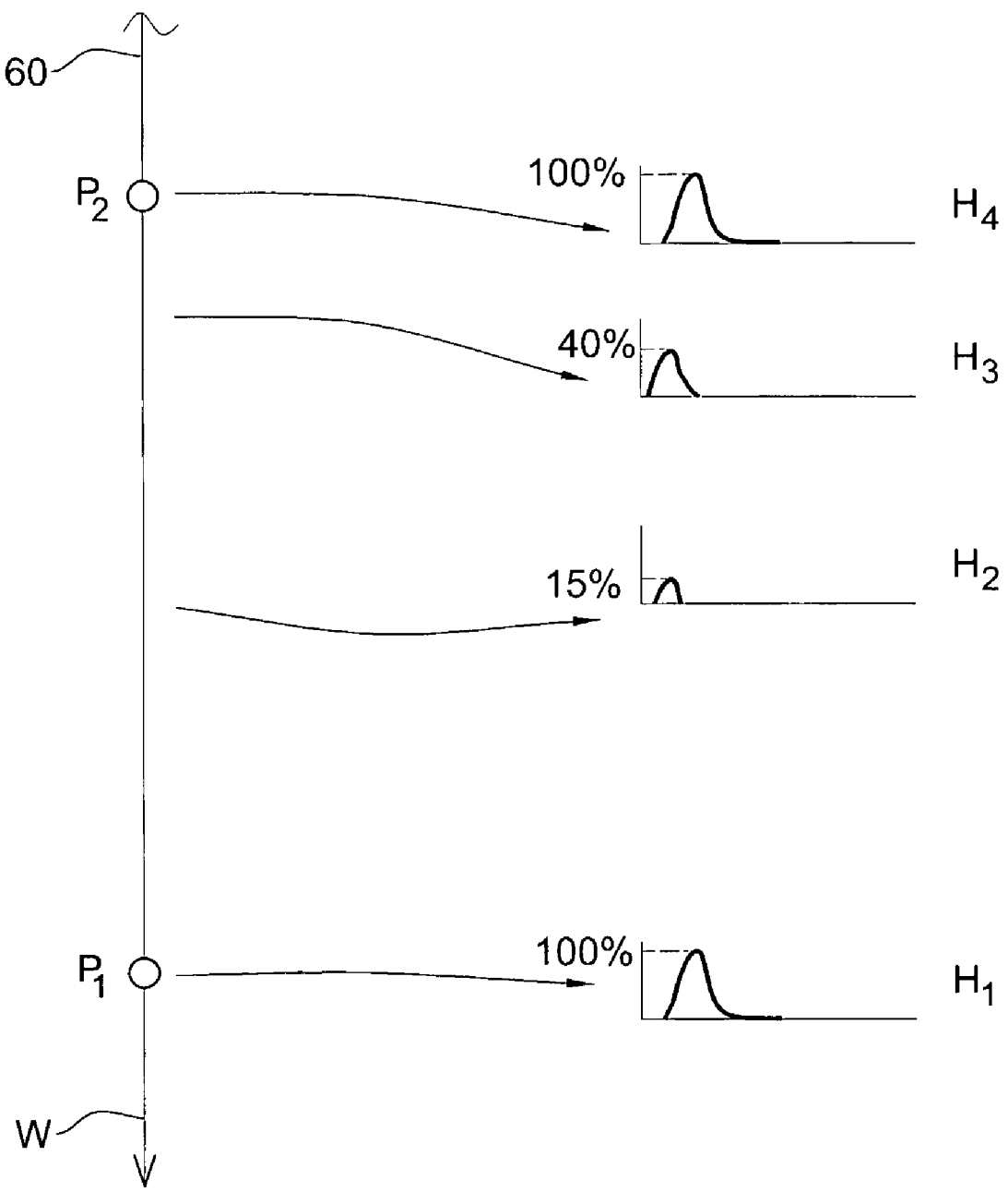
FIG. 6 is a schematic illustrations of an operation carried out according to an embodiment of the invention.

This is illustrated in FIG. 6: there is shown a fence portion 60 having a wire w and two posts $p_1$ and $p_2$. A plurality of contrast histograms $H_1$-$H_4$ are also shown, each representing a speckle intensity pattern of radiation reflected from different fence segments along a horizontal scanning direction. For example, $H_1$ and $H_4$ represent measurements taken in front of posts $p_1$ and $p_2$, respectively. $H_2$ represents a measurement taken in front of a wire segment located between poles $p_1$ and $p_2$, and $H_3$ represents a measurement taken in the vicinity of post $p_2$. Hence, it is possible to establish a description of the change of histogram parameters as a function of the distance between adjacent posts. It is also possible to determine the exact location of the vehicle with respect to the posts. Furthermore, it is possible to uniquely identify a post, e.g. by counting the posts during the movement of the vehicle along the fence.

Furthermore: additional information is available, either from external sources e.g. the absolute position of the vehicle (e.g. using GPS data, vehicle velocity data and more), or by the system and method of the invention, e.g. scanning angles, scanning height, distance between posts, distance between adjacent wires. By considering the additional information together with the intensity pattern generated by the detection units (e.g. elements 202-203 shown in FIG. 2), highly accurate segment localization is achieved. For example, along a 50 km long fence, a 10 cm segment can be located with resolution of only a few millimeters or less.

Figure 7:
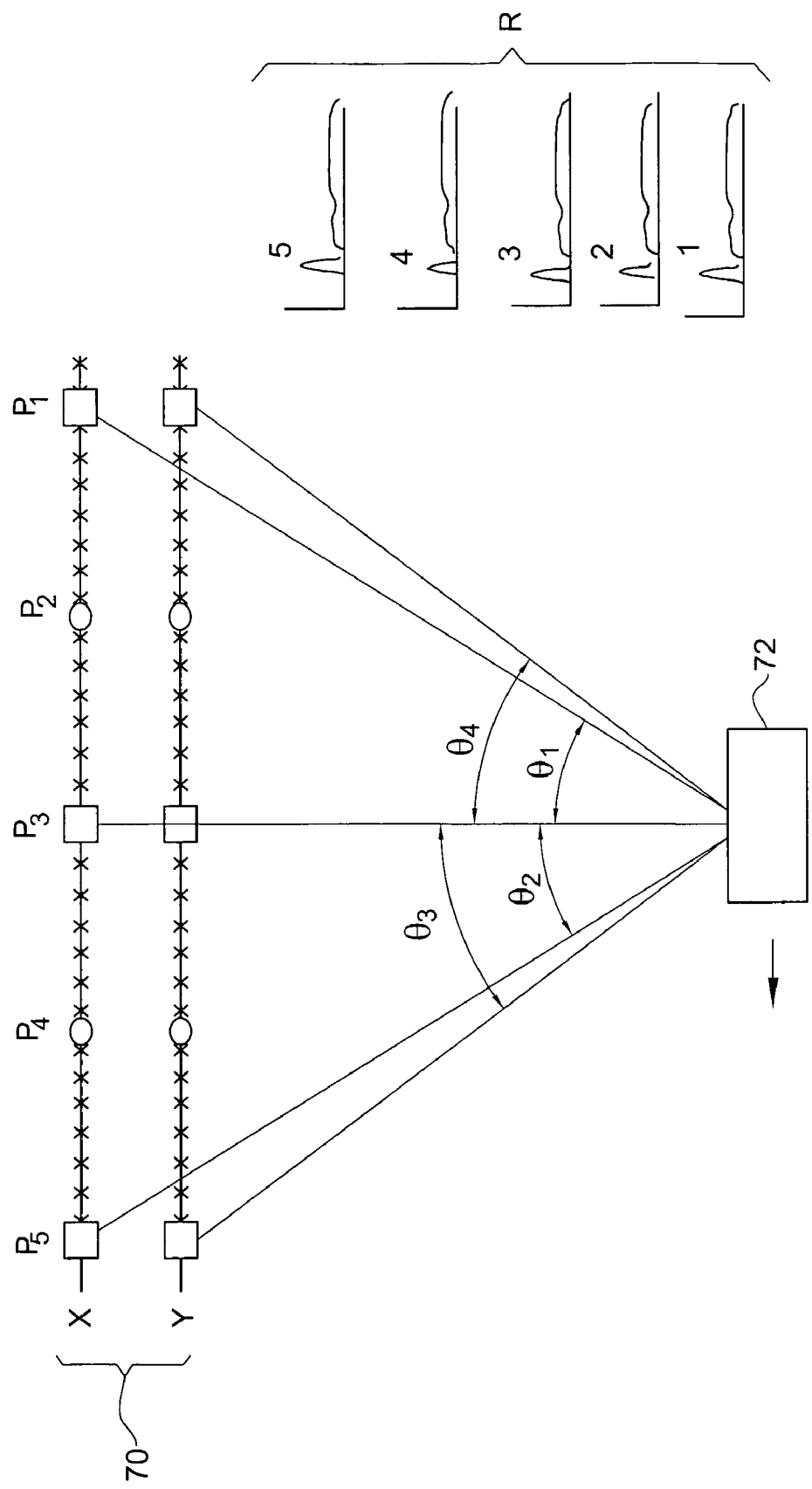
FIG. 7 is a schematic illustrations of an operation carried out according to an embodiment of the invention.

Turning now to FIG. 7: There is shown an illustration of a fence portion 70 having posts $p_1$-$p_5$ and two wires X and Y stretched between the posts, at different heights. According to the exemplified embodiment of the invention, the vehicle 72 comprises two detection units, namely units 202 and 203 shown in FIG. 2. Units 202 and 203 are laser scanning units, one—unit 202 operable along a horizontal scanning direction (that is, unit 202 scans along wires X and Y). The other unit—203—scans along a vertical direction, along posts $p_1$-$p_5$. The information gathered by both units 202 and 203 is processed to provide the 'occurrence data' and the 'location data'. This will now be illustrated:

A set of measurements R represents the updated speckle intensity pattern taken at a certain position of the vehicle 72 with respect to the fence. Following the processing discussed with reference to FIG. 6, highly accurate position information is available, and the updated speckle intensity pattern is segmented and correlated with substantially identical segmentation of the reference model.

Scanning angles $\theta_1$-$\theta_4$ can be used to provide further 'occurrence data': $\theta_1$ represents the scanning angle to $p_1$, taken along wire X. $\theta_4$ represents the scanning angle to the same post—$p_1$, taken along wire Y. The difference $\theta_1$-$\theta_4$ hence characterizes the inclination of $p_1$. The difference $\theta_1$-$\theta_4$ as measured at the provisioning operation is stored and forms part of the reference model. The difference $\theta_1$-$\theta_4$ is also determined based on the updated speckle intensity pattern. A discrepancy between the reference and updated values of difference $\theta_1$-$\theta_4$ is considered as an alteration which may indicate a bend of post $p_3$. The same considerations may be applied based on values of differences $\theta_1$-$\theta_2$, $\theta_2$-$\theta_3$, and other parameters.

To summarize, the present invention provides for highly accurate localization of fence segments, by associating each segment with a 'location data'. The location data is regenerated per operation of the system, and correlated substantially to the same segment. Each segment is further associated with 'occurrence data' indicating the occurrence of an alteration. According to the embodiment of the invention shown in FIG. 2, two laser scanners are employed to generate both data sets—the location data and the occurrence data are generated based on the speckle intensity pattern of the radiation reflected from the scattering elements of the fence. In other words, the invention provides for a system for mapping the fence by segmenting it and associating each segment with data indicative of the location of the segment and data indicative of the occurrence of an alteration in the segment.

According to an embodiment of the invention, the intensity pattern (e.g. the pattern generated by detection unit 202 shown in FIG. 2) is collected over a longer time period, and therefore the radiation received at the detection unit is reflected not only (or mainly) from the scattering elements of the fence, but also from behind the fence and through the openings. Hence, processing of the intensity pattern yields a three dimensional mapping of the structure surface and the space behind it.

According to another embodiment of the invention, at least one laser scanner is employed, together with a hologram scanning system. In this embodiment, hereinafter referred to as 'the hologram embodiment', the speckle intensity pattern generated by the laser scanner is used to generate the location data and occurrence data, as detailed above with reference to FIGS. 3a-3b to FIG. 7. The hologram scanner is used for generating data considered in constituting the 'occurrence data'. More specifically, in the hologram embodiment, the reference model includes, inter-alia, data indicative of at least one hologram of a typical, expected alteration. The hologram scanner generates data indicative of an updated hologram of the segment. By comparing the updated data with the stored reference data, the occurrence of the alteration could be determined. Note however, that the hologram scanner is thus limited to detect a limited set of alterations, only those having a reference hologram. This limitation may be overcome by assessing indications generated by the hologram scanner with information available e.g. from the speckle scanning system.

Figure 8:
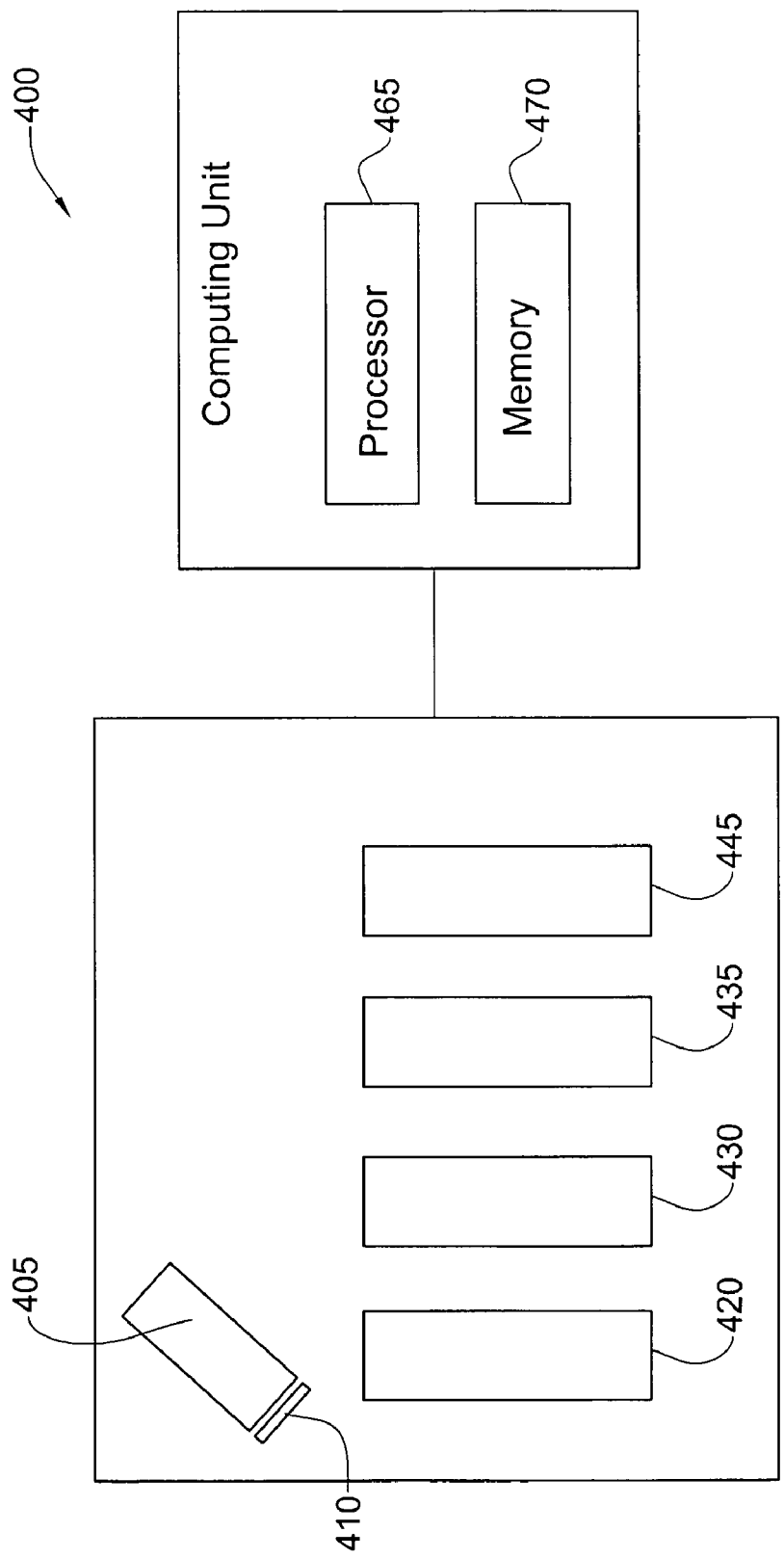
FIG. 8 is a schematic illustration of a system according to an embodiment of the invention.
Figure 9:
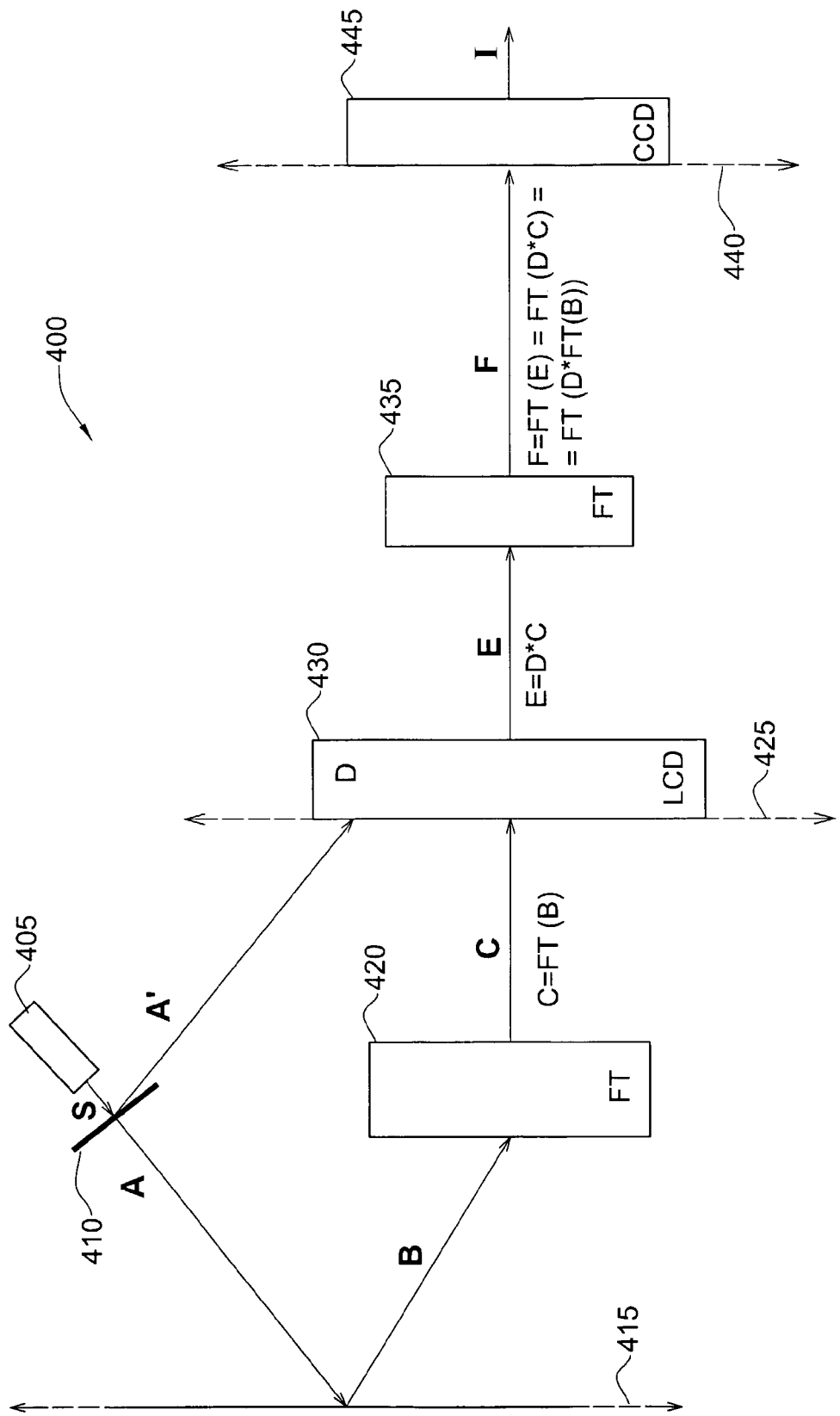
FIG. 9 is a schematic illustrations of an operation carried out by the system illustrated in FIG. 8 according to an embodiment of the invention.

The configuration and operation of the hologram scanner will now be detailed with respect to FIGS. 8 and 9: FIG. 8 is a schematic block diagram of a hologram detection unit 400 according to an embodiment of the invention. Unit 400 may constitute unit 103 shown in FIG. 1). Unit 400 comprises, inter-alia, the following elements: laser source 405, e.g. pulsed YAG laser operating in the near IR field; splitter 410; a first optic arrangement 420; hologram model 430 e.g. a film, an LCD panel and the like, for reconstructing a hologram; a second optic arrangement 420; a CCD element 445 or like elements. The hologram unit 400 further comprises or is coupled to a processor 465 and memory 470 (which could be realized by the computing unit shown 10 in FIG. 2).

FIG. 9 is a schematic illustration of a hologram unit according to an embodiment of the invention. Ray S coming from laser source 405 is split by splitter 410 to rays A and A'. Ray A impinges the scanned portion of the fence located at the object plane 415 and reflected therefrom as ray B. Passing through the first optic arrangement 420, ray C is indicative of a Fourier transform of ray B in a transformation plane 425:

$$C = FT(B) \quad (1)$$

Ray A', coherent with ray C, also impinge plane 425, where it reconstructs the hologram D carried by hologram model 430. Therefore, ray E is indicative of the combination of the reconstructed hologram D with ray C which is indicative of the updated state of the fence:

$$E = D \times C \quad (2)$$

Passing through the second optic arrangement, ray F is indicative of a Fourier transform of ray E in a correlation plane 440:

$$F = FT(E) = FT(C \times D) = FT(FT(B) \times D) \quad (3)$$

Hence, ray F is indicative of a correlation between an updated state of the fence—this information is carried by ray C, and a reference model—the information carried by hologram D. Therefore, the intensity pattern of ray F—detected by CCD 445, indicates the correlation between the updated state of the fence and the reference model. By providing a hologram reference model of one expected alteration, e.g. of a cut-off, the detected intensity pattern will indicate if that specific alteration exists in the scanned portion. In case the reference model relates to a plurality of holograms, the detected intensity pattern will indicate whether no alteration exists, or that at least one from a plurality of expected alterations exists in the scanned portion.

Note that the use of the hologram detection unit is not limited to structures having scattering elements and openings between the elements. The detection principles described above with reference to FIGS. 8 and 9 are equally useful for detection of alterations in any type of structure, with necessary modifications. However, for practical applications, faster processing is yielded when applying hologram scanning to structures with smaller reflective face area, and for detecting a relatively small group of expected alterations.

Turning back to FIGS. 1 and 2, showing a detection-system with two or three detection units: several embodiments of the invention were presented above, namely, the 'double speckle scanning' embodiment—employing two laser scanners generating speckle intensity patterns; the hologram embodiment employing a speckle laser scanner and a hologram scanner; and the embodiment shown in FIG. 2, employing two speckle laser scanners with a video camera. It should be understood that the configuration of a detection system according to the invention is not limited by the exemplified configurations, and others are also applicable, with necessary modifications.

Thus, widely described, the present invention provides for a system for locating a physical alteration, if such exists, in a structure having a substantially planar surface comprising a plurality of elements capable of scattering electro-magnetic radiation and openings arranged between the elements, the system comprising:

a moving platform for providing relative motion of the system with respect to the structure (e.g. platform 100 shown in FIG. 1);

at least one source of coherent electro-magnetic radiation configured for illuminating at least a portion of said surface in its relative motion with respect to the structure (e.g. one source serving two speckle scanners, each detection unit having its own source);

at least a first and a second detection units each operable along a different collection direction and configured for collecting electro-magnetic radiation reflected from said at least a portion of the surface and for generating an intensity pattern of the reflected radiation indicative of an arrangement of the elements and openings (e.g. two speckle scanners with or with out a video camera, one speckle scanner with a hologram scanner);

a computing unit configured for generating a segmented map of the portion based on said intensity patterns, by associating each segment with location data indicative of the location of the segment and occurrence data indicative of an occurrence of the alteration, thereby allowing to compare said map to a reference model and determine the location of the alteration, if such exists. The reference model may include data generated by processing a speckle intensity pattern, a correlation (hologram) intensity pattern or a combination thereof.

Figure 10:
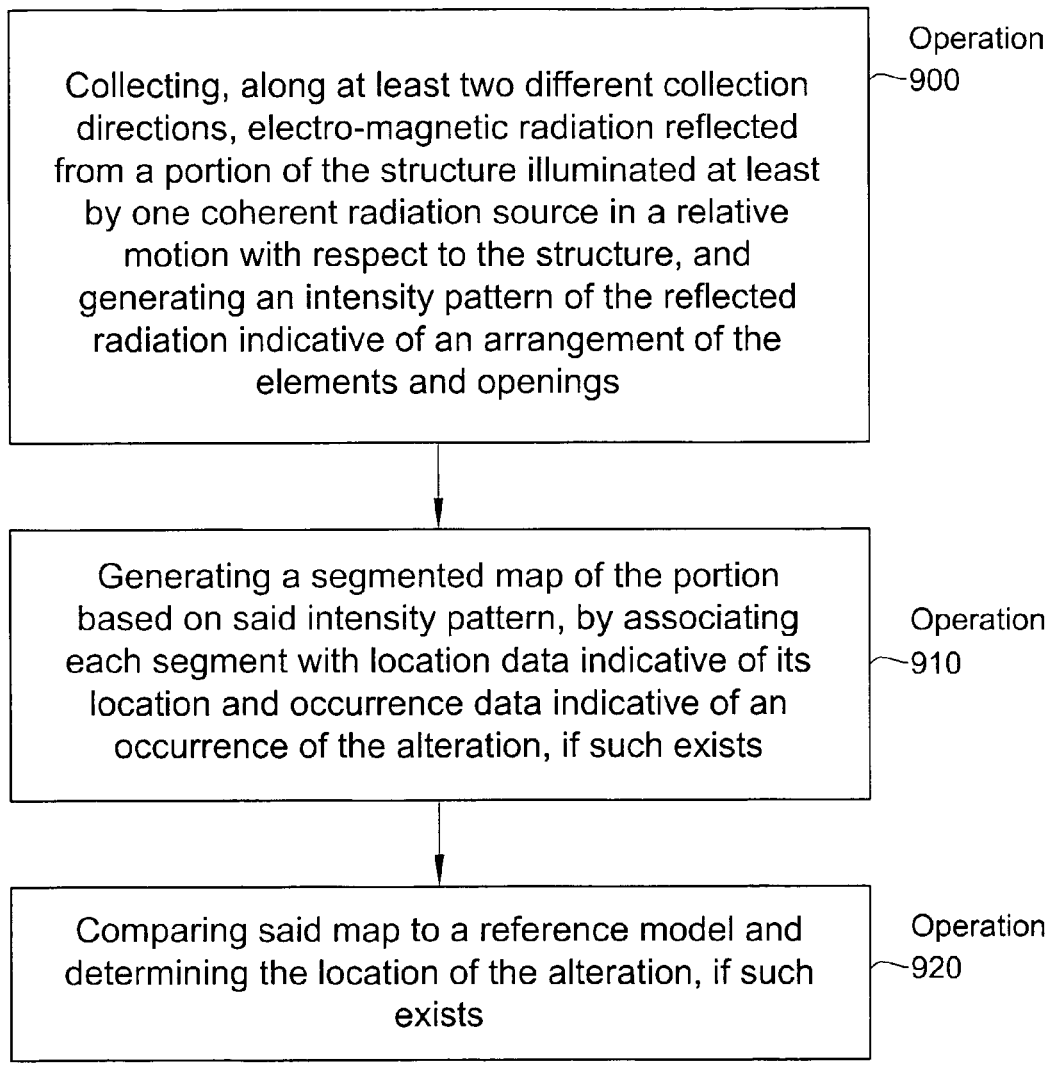
FIG. 10 is a flow chart showing a sequence of operations carried out according to an embodiment of the invention.

Reference is now made to FIG. 10, which is a flow chart of a sequence of operations 90 carried out in accordance with an embodiment of the invention, for detecting and locating an alteration in a structure having a substantially planar surface formed by a plurality of elements capable of scattering electro-magnetic radiation and openings arranged between the elements:

In operation 900: collecting, along at least two different collection directions, electro-magnetic radiation reflected from a portion of the structure illuminated at least by one coherent radiation source in a relative motion with respect to the structure, and generating an intensity pattern of the reflected radiation indicative of an arrangement of the elements and openings. As discussed above, the intensity pattern may be a speckle intensity pattern or a correlation (hologram) intensity pattern, or a combination thereof.

In operation 910: generating a segmented map of the portion based on said intensity pattern, by associating each segment with location data indicative of its location and occurrence data indicative of an occurrence of the alteration, if such exists.

In operation 920: comparing said map to a reference model and determining the location of the alteration, if such exists.

As discussed above with reference to FIGS. 3a-3b to 9, the reference model comprises, inter-alia, 'location data'—a segmented map of the fence generated based on information gathered at least by one speckle laser scanner, and 'occurrence data'. The reference model may be generated by one of the following operations: a provisioning operation of the system along the surface, a succession of provisioning operations of the system along the surface, a succession of previous operations of the system along the surface, and a combination of at least one provisioning operation of the system with at least one previous operation of the system along the surface. In the case of the hologram embodiment, the reference model further encompasses one or more holograms indicating one or more expected alterations.

Note that sequence of operations 900 could be carried out in an iterative manner, per a portion of the detected fence, during the motion of the detection vehicle along the fence. Furthermore, as discussed above with reference to FIG. 6, an attempt to penetrate or tamper with the fence may give rise to several alterations, which in turn may be detected by one or more detection units. According to an embodiment of the invention, there are provided predefined verification rules, for assessing various alteration indications. The verification rules may be applied in a fully automated, fully manned or semi-automated operation. The verification rules are applied by analyzing occurrence data associated with different segments.

As detailed above with reference to the 'double speckle embodiment' and the 'hologram embodiment', information generated by one detection unit is integrated with information gathered by the other one or more detection units. One aspect of this integration relates to the association of the 'occurrence data', generated at least by one unit, to a segment, based on the 'location data' generated at least by one of the other units. Another aspect relates to the generation of the 'occurrence data' by applying verification rules for assessing indications about possible alterations, generated by one or more units.

According to an embodiment of the invention, a full image of the fence portion is generated (e.g. by video camera 204 shown in FIG. 2), and information relating to the occurrence of an alteration is superimposed onto the image, e.g. by correlating the video image with the segmented map of the fence. Furthermore, by correlating the video image with the segmented map of the fence, additional occurrence data may be obtained by processing the video image. For example, in case an indication of an alteration e.g. a cut-off is detected, an additional image processing is triggered, e.g. to look for supporting or contradicting indications. For example, in the vicinity of the cut-off there is expected to be found a change in the shading of certain fence elements, e.g. due to loss of some dust layers.

Figure 11:
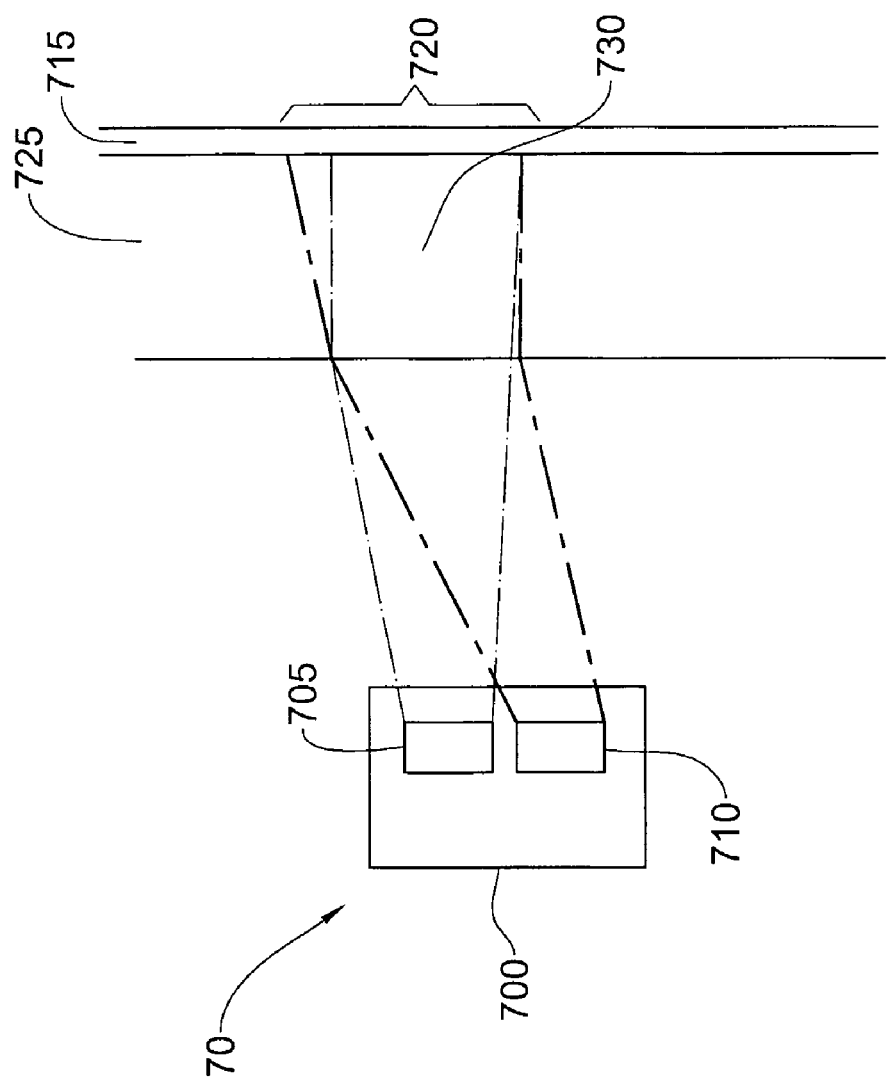
FIG. 11 is a schematic illustration of a system according to another embodiment of the invention.

According to an embodiment of the invention illustrated in FIG. 11, there is provided a system 70, comprising, inter-alia, a moving platform 700 and two detection systems mounted onboard—system 705 for detecting an alteration in a fence 715 (as described above e.g. with reference to FIG. 2), and system 710 for detecting a road 725, according to various known methods. During movement of the platform 700 along the fence, both systems detect a portion of the fence and a corresponding portion of the road. According to an embodiment of the invention, information gathered by system 705 is used to analyze information gathered by system 710. According to another embodiment of the invention, information gathered by system 710 is used to analyze information gathered by system 705. In other words, the verification rules discussed above with reference to FIG. 10 may be applied based on information acquired externally to system 705. Furthermore, the information gathered by the system 705 could be available for system 710 and any other system located onboard the moving platform, as well as for a remote system.

According to an embodiment of the invention, the operation of the detection system is fully automated. According to other embodiments, an operator is involved with various aspects of operations, e.g. assessing indications of possible alterations, reviewing external information, responding to detected alterations, and more.

In the embodiment illustrated in FIG. 2, one computing unit (element 206) serves all components of the detection system. It should be understood that the invention is not limited by the illustrated configuration and many others are possible, without departing from the scope of the invention, with necessary modifications.

In the above description, the relative movement between the detection system and the fence is implemented by mounting the system onboard a moving platform (element 100 in FIG. 1). According to an embodiment of the invention, platform 100 is an all-terrain vehicle. According to another embodiment, the platform 100 is further equipped with obstacle-avoidance and self-guidance systems, and more. It should be understood that the invention is not limited by the illustrated configuration and many others are possible within the scope of the present application. For example, relative movement between the detection system and the detected structure may be provided by moving the structure with respect to the detection system.

In the above description, the invention is described mainly with reference to detection of alterations in a fence—which is a continuous structure. It should be understood that the invention is not limited to continuous structures. The principles of the present invention are useful for detecting an alteration in a succession of discrete structure portions.

The invention claimed:

1. A scanning system for locating a physical alteration, if such exists, in a structure having a substantially planar surface comprising a plurality of elements capable of scattering electro-magnetic radiation and openings arranged between the elements, the system comprising:
   a moving platform for providing relative motion of the system with respect to the structure;
   at least one source of coherent electro-magnetic radiation configured for illuminating at least a portion of said surface in its relative motion with respect to the structure;
   at least a first and a second detection unit each operable along a different collection direction and configured for collecting electro-magnetic radiation reflected from said at least a portion of the surface and for generating a speckle intensity pattern of the reflected radiation indicative of an arrangement of the elements and openings;
   a computing unit configured for generating a segmented map of the portion based on said intensity patterns, by associating each segment with location data indicative of the location of the segment and occurrence data indicative of an occurrence of the alteration,
   thereby allowing to compare said map to a reference model and determine the location of the alteration, if such exists.

2. The system according to claim 1 wherein said source, said first and second detection units and said computing units are accommodated onboard the moving platform.

3. The system according to claim 1 wherein said first and second detection units are further operable for communicating a signal indicative of the intensity pattern to a remote computing unit, via a communication unit.

4. The system according to claim 1 wherein said source of coherent electro-magnetic radiation is a laser source having a wavelength substantially in the order of the irregularity that characterizes the scattering element material, or less.

5. The system according to claim 1 wherein the first detection unit is a video camera system adapted to provide at least one video image of the illuminated portion.

6. The system according to claim 1 wherein the computing unit is further configured for processing intensity pattern corresponding to radiation reflected through the openings, thereby allowing partial three-dimensional mapping of a space behind the surface of the structure.

7. The system according to claim 1 wherein the scattering elements are arranged in a periodic design which can be identified based on variations in the intensity pattern generated by at least the first or second detection units; and wherein the variations are used in generating said location data.

8. The system according to claim 7 wherein the at least one source of electro-magnetic radiation is configured for illuminating the at least a portion of the surface in accordance with predefined illumination plan corresponding to the periodic design of the structure.

9. The system according to claim 7, wherein the periodic design comprises a plurality of substantially horizontal elements and a plurality of a substantially vertical elements, and wherein one of said different collection directions is substantially horizontal and the other collection direction is substantially vertical.

10. The system according to claim 1 wherein the reference model includes a reference collection of data sets, each associated with a segment of the structure and including a reference occurrence data.

11. The system according to claim 1 wherein the computing unit is further configured for applying at least one predefined verification rule by analyzing occurrence data associated with different segments.

12. The system according to claim 1 further comprising a display, wherein the first detection unit is a video camera system adapted to provide at least one video image of the illuminated portion, and wherein said computing unit is further configured for superimposing indications of the location and occurrence of the alteration, if such exists, with an image of the portion captured by the video camera, and for feeding the display with a corresponding signal.

13. The system according to claim 1 wherein said computing unit is configured for receiving instructions provided by an operator.

14. A scanning method for detecting and locating an alteration in a structure having a substantially planar surface formed by a plurality of elements capable of scattering electro-magnetic radiation and openings arranged between the elements, the method comprising:
   a. collecting, along at least two different collection directions, electro-magnetic radiation reflected from a portion of the structure illuminated at least by one coherent radiation source in a relative motion with respect to the structure, and generating a speckle intensity pattern of the reflected radiation indicative of an arrangement of the elements and openings;

b. generating a segmented map of the portion based on said intensity pattern, by associating each segment with location data indicative of its location and occurrence data indicative of an occurrence of the alteration, if such exists, thereby allowing to compare said map to a reference model and determine the location of the alteration, if such exists.

15. The method according to claim 14 further comprising:
c. comparing said map to a reference model and determining the location of the alteration, if such exists.

16. The method according to claim 15 further comprising:
d. applying at least one predefined verification rule by analyzing occurrence data associated with different segments.

17. The method according to claim 16 further comprising:
e. superimposing indications of the location and occurrence of the alteration, if such exists, with an image of the portion captured by a video camera.

18. The method according to claim 14 wherein said collecting further comprises collecting electro-magnetic radiation reflected from said portion further illuminated by a non-coherent radiation source in a relative motion with respect to the structure.

19. The method according to claim 14 wherein said reference model includes, for each segment, an occurrence data generated based of one of the following:
a provisioning operation;
a succession of provisioning operations;
a succession of previous operations and
a combination of at least one provisioning operation with at least one previous operation.

20. A scanning method for detecting and locating an alteration in a structure having a substantially planar surface formed by a plurality of elements capable of scattering electro-magnetic radiation and openings arranged between the elements, the method comprising:

a. collecting, along at least two different collection directions, electro-magnetic radiation reflected from a portion of the structure illuminated at least by one coherent radiation source in a relative motion with respect to the structure, and generating a speckle intensity pattern of the reflected radiation indicative of an arrangement of the elements and openings;

b. generating a segmented map of the portion based on said intensity pattern, by associating each segment with location data indicative of its location and occurrence data indicative of an occurrence of the alteration, if such exists, c. comparing said map to a reference model and determining the location of the alteration, if such exists.

d. applying at least one predefined verification rule by analyzing occurrence data associated with different segments; and e. superimposing indications of the location and occurrence of the alteration, if such exists, with an image of the portion captured by a video camera.

21. The method according to claim 20 wherein at least operation c or d are completed based on instructions received from an operator.

22. The method according to claim 21 wherein said collecting further comprises collecting electro-magnetic radiation reflected from said portion further illuminated by a non-coherent radiation source in a relative motion with respect to the structure.

* * * * *